United States Patent
Bukin

(10) Patent No.: US 7,275,437 B2
(45) Date of Patent: Oct. 2, 2007

(54) ACOUSTICAL CELL FOR MATERIAL ANALYSIS

(75) Inventor: Vitaly Bukin, Dublin (IE)

(73) Assignee: Ultrasonic Scientific Ltd., Dublin (IE)

( * ) Notice: Subject to any disclaimer, the term of this patent is extended or adjusted under 35 U.S.C. 154(b) by 0 days.

(21) Appl. No.: 10/498,227

(22) PCT Filed: Dec. 10, 2002

(86) PCT No.: PCT/EP02/13974

§ 371 (c)(1),
(2), (4) Date: Aug. 14, 2004

(87) PCT Pub. No.: WO03/052402

PCT Pub. Date: Jun. 26, 2003

(65) Prior Publication Data
US 2005/0011264 A1    Jan. 20, 2005

(30) Foreign Application Priority Data
Dec. 14, 2001   (EP) ................................. 01310459

(51) Int. Cl.
*G01N 29/024* (2006.01)
(52) U.S. Cl. .................. 73/597; 73/24.06; 73/633
(58) Field of Classification Search .............. 73/597, 73/579, 590, 644, 64.53, 61.79, 61.49, 61.48, 73/632, 645, 24.06, 633
See application file for complete search history.

(56) References Cited

U.S. PATENT DOCUMENTS

| | | | |
|---|---|---|---|
| 3,344,658 A * | 10/1967 | Heisig et al. ............... 73/19.03 |
| 3,974,681 A | 8/1976 | Namery | |
| 4,735,906 A | 4/1988 | Bastiaans | |
| 4,770,043 A * | 9/1988 | Cobb et al. ................... 73/597 |
| 5,542,298 A * | 8/1996 | Sarvazian et al. ............. 73/597 |
| 5,768,937 A * | 6/1998 | Wajid et al. ................ 73/24.06 |
| 5,836,200 A * | 11/1998 | Belonenko et al. ........ 73/61.79 |
| 5,983,723 A * | 11/1999 | Buckin et al. ................. 73/633 |
| 6,199,423 B1 | 3/2001 | Logue et al. | |
| 6,764,215 B2 * | 7/2004 | Meyler et al. ................. 374/32 |
| 6,809,315 B2 * | 10/2004 | Ellson et al. ................ 250/288 |
| 6,932,097 B2 * | 8/2005 | Ellson et al. ................... 137/2 |
| 2004/0020294 A1 * | 2/2004 | Buckin ........................ 73/597 |

FOREIGN PATENT DOCUMENTS

DE    3420794 A1 *    4/1984

* cited by examiner

Primary Examiner—Hezron Williams
Assistant Examiner—Jacques M. Saint-Surin

(57) ABSTRACT

An acoustical cell for analysis of materials by measuring parameters of acoustical resonanace. The cell comprises a main frame and an electroacoustical transducer assembly. The main frame includes at least one interstice and has substatially parallel exterior surfaces that engage, in use, with walls to define a resonant cavity into which a specimen for analysis is placed in use. The electroacoustical transducer assembly is acoustically coupled to at least one of the walls and comprises at least one electroacoustical transducer.

12 Claims, 2 Drawing Sheets

ACOUSTICAL CELL FOR MATERIAL ANALYSIS

The present invention relates generally to material analysis, and more particularly to a device in which acoustic wave fields may be generated in material specimens and the frequency dependencies of the amplitude, phase or impedance of these fields may be analysed.

In acoustical cell technology it is known to make acoustic measurements by placing a specimen in a chamber and generating acoustical resonances within the chamber. These acoustical resonances are generally created by mechanical vibrations which set up wave patterns in the sample. Measurement of these wave patterns leads to a characterisation of the interaction between the acoustical wave and the sample and thus a high resolution evaluation can be made of the properties of the material. This technique has the advantage that measurements can take place on very small samples. The precision geometry of the chamber is an important factor in both the precision of the measurements obtained and also in the cost of manufacture of the cell. The cell geometry must also be chosen to minimise the creation of air bubbles within the cell, for example. However, a consideration such as this may be in conflict with the requirement for mathematically simple shapes, which simplify analysis, for the walls of the chamber. Other considerations that need to be taken into account in the choice of geometry for the cell are factors such as the chemical resistance of the walls, effective cleaning procedures and effective stirring of a specimen. Furthermore, environmental factors such as heat expansion play a major role in altering the geometry and this must be considered seriously in the choice of materials for cell construction. It can therefore be difficult to provide an acoustical cell that meets these criteria, yet which is also cost effective and which does not require complex support equipment to operate.

The walls contribute to the measured parameters of the cell itself. For precision and high resolution it is desirable to reduce the contribution of the walls by having thinner walls. As various engineering techniques allow vessels to be engineered with thinner and thinner walls there is increasingly a problem caused in that these walls will also transmit external vibrations and may warp under the temperature and pressure variations caused both by the sample and the surroundings.

Pressure variations within a sample are also prone to cause warping of the cell, this is particularly relevant when the sample is undergoing a reaction within the cell and may be emitting a gas and therefore increasing the pressure within the cell.

The present invention seeks to overcome some of the above mentioned problems and provide a cell which is cost effective and simple to operate.

According to the present invention there is provided an acoustical cell for analysis of materials by measuring parameters of acoustical resonance, the cell comprising:

a main frame including at least one interstice and having exterior surfaces that engage, in use, with walls to define a resonant cavity into which a specimen for analysis is placed in use, and an electroacoustical transducer assembly acoustically coupled to at least one of the walls and comprising at least one electroacoustical transducer.

Preferably the cell further comprises a supporting frame substantially encasing the main frame and the walls. The supporting frame and the walls may be fabricated as a single block and may be formed from the same material.

Preferably, the main frame, walls and supporting frame, if provided, are formed of an optically transmissive material to allow optical parameters to be measured.

The space between the supporting frame and the walls may be filled with fluid, in use.

The walls may be substantially planar, spherical or cylindrical to minimise diffraction losses.

Preferably, the transducer is biassed to remain in direct or indirect contact with the walls.

The cell may further comprise a stopper to avoid sample evaporation in use.

Preferably, the at least one interstice further comprises a channel for the injection of fluids.

Preferably, the at least one interstice is arranged such that a sample can flow, in use, therethrough.

The presence of a supporting frame and especially the provision of the supporting frame and central frame being formed of one block, even of one material reduces the incidence of warping of the cell when the cell is exposed to variations of temperature, pressure on mechanical force applied thereto.

Examples of the present invention will now be described with reference to the drawings, in which.

Figure 1:
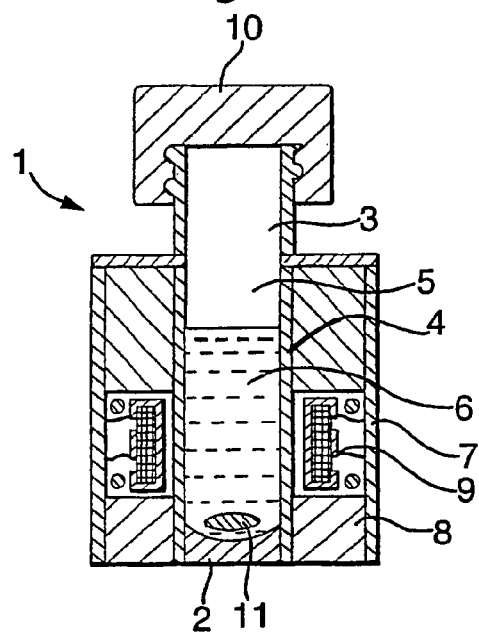
FIG. 1 shows a cross sectional view of an example of the present invention.

FIG. 1 shows a cell 1 according to the present invention. The cell 1 comprises a main frame 2, shown in FIG. 3 opposite surfaces 20 and 22 and at least one interstice 3 having opposite ends 24 and 26 which extend between the surfaces 20 and 22. Inner walls 4 having left and right marginal edges 28 and top and bottom marginal edges 30 in use with walls 4 engage the surfaces 20 and 22 (see FIG. 1) to define a resonant cavity 5 in which a sample 6 may be placed. The resonant cavity 5 is surrounded by a supporting frame 7 comprising a pair of outer walls 40 and 42, a top side wall 44 and a pair of lateral side walls 46. The outer walls 40 are joined at their marginal edges to the corresponding marginal edges of the inner walls 4 by the top side wall 44 and lateral side walls 46 forming A gap 8 between the walls 4 and 40 which frame 7 and the resonant cavity 5 accommodates at least one transducer 9. A stopper 10 is provided. A stirring magnet 11 is optionally provided within the main frame 1.

The at least one transducer 9 is attached to at least one of the walls 4 to generate acoustical resonance. The transducer may be sealed to prevent ingress of condensation, and may be surrounded by inert gas to improve control of its parameters. The detection of the resonance may take place through measuring the electrical characteristics of the transducer 9 or by measuring the electrical characteristics of a second transducer 9 optionally attached to the same or a second wall 4 of the resonant cavity 5. Although these acoustical resonances are generally created by mechanical vibrations which set up standing wave patterns if the attenuation coefficient of the material is very high then an acoustical resonance cannot be formed and in this case the continuous wave itself may be employed to evaluate the acoustical parameters of the specimen. The walls 4 may be substantially planar parallel walls, as shown, or alternatively they may be, for example, spherical or cylindrical in shape in order to provide a cavity shape that minimises diffraction at low frequencies. This feature of the walls 4 may also have the added benefit of aiding the filling of the resonant cavity 5 with the sample 6 prior to analysis.

The supporting frame 7 is provided to overcome the problems associated with the trade off between thin walls which, are desirable for high resolution analysis, and the problem of instability and possible warping of thin walls. In order to overcome this problem it is envisaged that the central frame, supporting frame and the walls may be made from a single block. Furthermore, this single block may be formed from one material such as quartz or glass. This approach has the advantage that the module has fewer internal parts that need cleaning and reassembling. High precision optical engineering has, for some time now, provided high precision objects in optically transmissive materials and the present invention draws on this expertise in order to provide a cell 1 for high precision acoustical measurements.

In this example, the electrical connections serving the transducers are grouped together so that only one connection to the cell 1 as a whole is needed regardless of the number of transducers. This, combined with a single block configuration for the cell 1 itself, results in a cell 1 which operates as a plug-in module providing ease of connection and removal of the module for cleaning or refilling purposes.

Furthermore, the gap 8 between the supporting frame 7 and the resonant cavity 5 may be used to control the conditions within the resonant cavity 5 by filling the gap 8 with, for example, an inert gas if the sample 6 is volatile. In addition there may be an outer shell (not shown) attached to the supporting frame 5 which may form a water bath to control the temperature of the sample 6. Other forms of temperature control are possible.

The electroacoustical transducer 9 can be attached to one of the walls 4 permanently or via a highly viscous and/or elastic layer, thus avoiding deformation of the walls 4 and the transducer 9 with increased temperature due to the different heat expansion coefficients of the transducer 9, the walls 4 and the material connecting them. In addition an elastic element such as a spring or O-ring can be used to bias a non-permanently attached electroacoustical transducer 9 against the walls 4.

Given the precise nature of the measurements being made in the cell 1, the issue of the heat expansion coefficients of the various components is often important and therefore the supporting frame 7 and the walls 4 may be formed as a single block to reduce this problem and may be formed from the same materials which may be the same as that forming the transducer.

The magnet 11 housed in the base of the main frame 2 allows the sample 6 to be stirred when used in conjunction with a magnetically actuated stirring mechanism (not shown). The stopper 10 is provided in order to overcome the problem of sample evaporation from the cell 1.

The example may further be supplied with means (not shown) by which a fluid may be injected into the resonant cavity 5 thereby to mix with the sample 6. Thus, such an arrangement can be used, for example, for titration.

Figure 2:
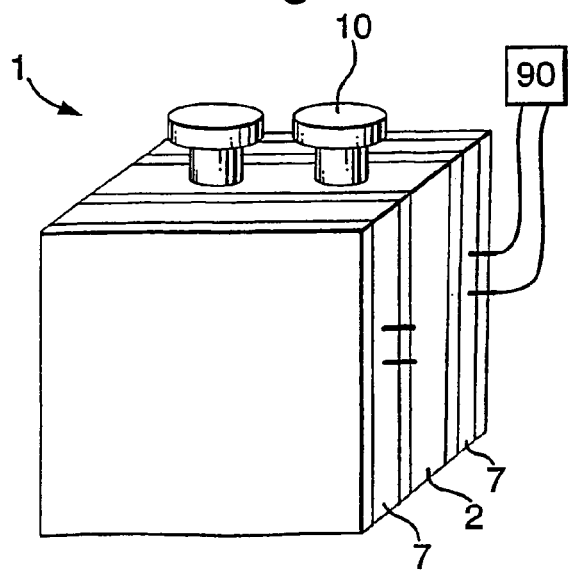
FIG. 2 shows a cell according to the present invention comprising two interstices.

FIG. 2 shows the exterior of cell 1 with the inlets of the two interstices 3 closed by stoppers 10. The advantage of having two interstices 3 is that parallel measurements may be made of two separate substances under the same conditions allowing precision measurement of differential effects.

Figure 3:
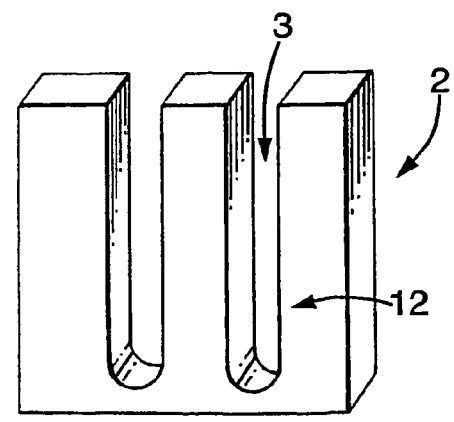
FIG. 3 shows a front view of a main frame employed in the example of FIG. 2.

FIG. 3 shows the main frame 2 with two interstices 3 that is used in the example of FIGS. 1 and 2. The front 12 and back (not shown) walls are substantially parallel so that they can engage easily with the walls 4 to form the resonant cavity 5. More interstices could be provided dependent upon the application.

Figure 4:
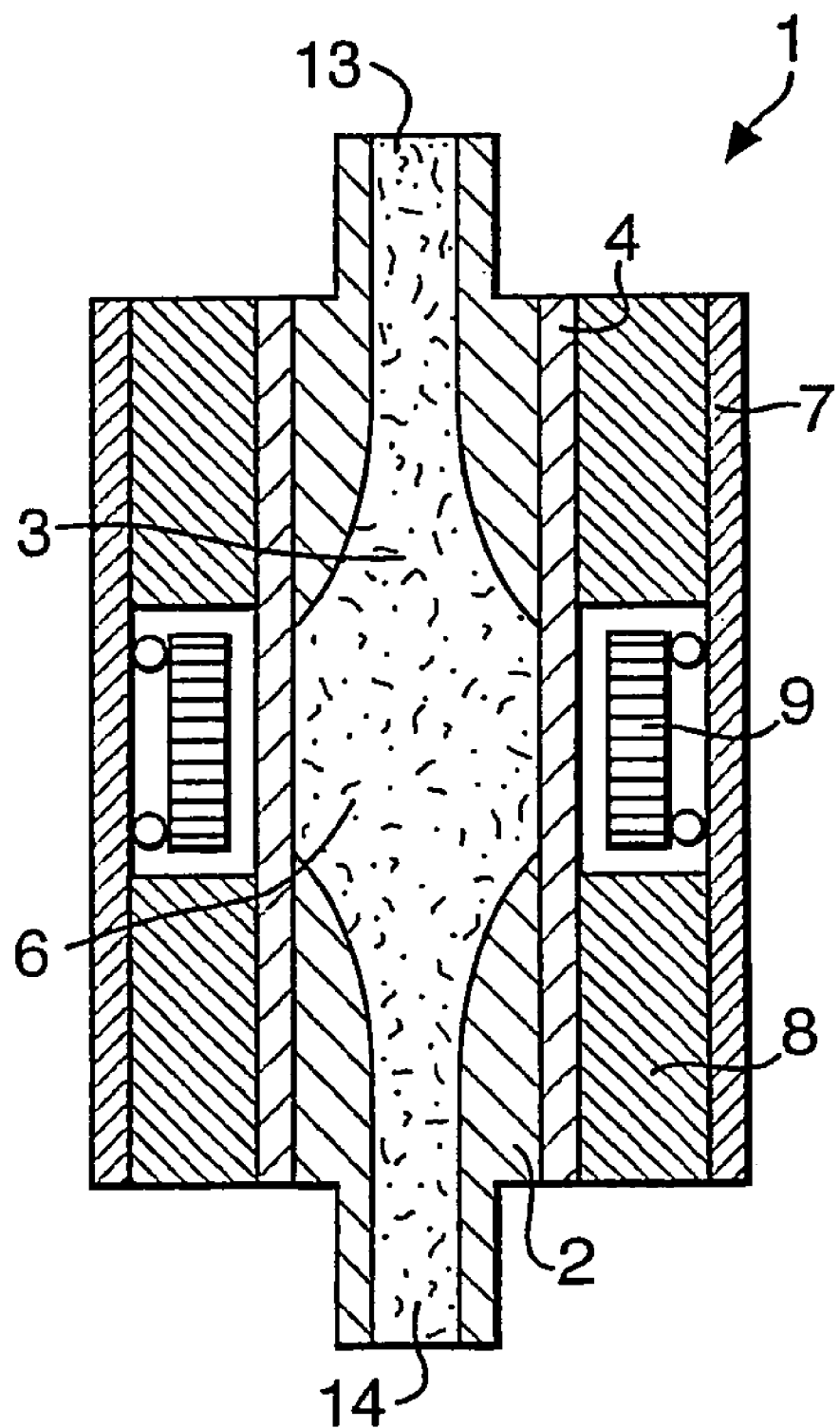
FIG. 4 shows a cross sectional view of a second example of the present invention.

FIG. 4 shows an alternative configuration of the present invention. The main frame 2 in this example has an inlet 13 and an outlet 14. Components that correspond to those in the earlier example are numbered identically. This configuration allows measurements to be taken during flow-through of material with a constant flow rate.

Another problem resulting from the precise nature of the measurements being made in the cell 1 is that of background noise. In order to reduce and quantify this problem it may be advantageous to employ a main frame 2 with two interstices 3 using a flow through configuration and repeat the measurements under the same pressure conditions in order to quantify the noise present in the system.

The invention claimed is:

1. An acoustical cell having a resonant cavity for receiving a specimen for analysis comprising:
   a layered structure including a main frame comprising a block including having oneopposite lateral surfaces and an interstice having open lateral ends extending between the opposite lateral surfaces; and having exterior surfaces that engage in use with walls
   an inner wall having marginal edges for engaging each corresponding lateral surface for closing the end of the open ends of the interstice to thereby define the resonant cavity for receiving the specimen;
   a supporting frame comprising an outer wall for each corresponding inner wall, having marginal edges, said outer wall being disposed in spaced relation with each inner wall; and side wall portions connecting the margins of the inner and outer walls to form a partially closed space therebetween; and
   an electro-acoustical transducer assembly including an electro-acoustical transducer acoustically coupled to at least one of the inner walls.

2. An acoustical cell according to claim 1, wherein the exterior surfaces of the main frame are substantially parallel.

3. An acoustical cell according to claim 2, wherein the cell has conduits for receiving temperature controlling fluid.

4. An acoustical cell according to claim 1, wherein the layered structure including the supporting frame and the inner-walls are fabricated as a block.

5. An acoustical cell according to claim 1, wherein the inner walls and outer walls are substantially planar.

6. An acoustic cell according to claim 1, wherein the transducer is biased to contact the walls.

7. An acoustical cell according to claim 1, wherein the main frame, the inner walls and supporting frame are formed of an optically transmissive material optical parameters to be measures.

8. An acoustical cell according to claim 1, further comprising a stopper to evaporation use close the cavity.

9. An acoustical cell according to claim 1, wherein the at interstice further comprises a channel for the injection of fluids.

10. An acoustical cell according to claim 1, wherein the at least one interstice has a flow channel for directing the sample into and out of the chamber.

11. An acoustical cell according to claim 1 wherein the layered structure is formed of chemically resistant materials.

12. An acoustical cell according to claim 1, wherein the transducer is movably coupled to the wall.

* * * * *